US00PP28872P3

(12) United States Plant Patent
Randag

(10) Patent No.: US PP28,872 P3
(45) Date of Patent: Jan. 9, 2018

(54) VARIETY OF CALLA LILY PLANT NAMED 'HAVANA'

(50) Latin Name: *Zantedeschia sprengeri*
Varietal Denomination: Havana

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 59 days.

(21) Appl. No.: 14/998,462

(22) Filed: Jan. 6, 2016

(65) Prior Publication Data

US 2016/0212923 P1 Jul. 21, 2016

Related U.S. Application Data

(60) Provisional application No. 62/125,226, filed on Jan. 15, 2015.

(51) Int. Cl.
*A01H 5/02* (2006.01)

(52) U.S. Cl.
USPC ..... Plt./490

(58) Field of Classification Search
USPC ..... Plt./490
CPC ..... A01H 5/0272
See application file for complete search history.

*Primary Examiner* — Kent L Bell
(74) *Attorney, Agent, or Firm* — The Webb Law Firm

(57) ABSTRACT

'Havana' is a new variety of calla lily plant having inflorescences with a large, orange/red bicolored spathe that produces 3-10 inflorescences per tuber. The height of the top of an inflorescence above the soil can reach up to 49 cm, and the leaves are dark green with transparent maculations present and have a leathery texture.

2 Drawing Sheets

Botanical classification: *Zantedeschia sprengeri*.
Varietal denomination: 'HAVANA'.

BACKGROUND OF THE NEW PLANT

The present invention comprises a new and distinct cultivar of calla lily, botanically known as *Zantedeschia sprengeri* and hereinafter referred to by the cultivar name 'Havana'.

'Havana' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of *Zantedeschia sprengeri* 'Mercedes' (female parent, unpatented) with a *Zantedeschia sprengeri* selection referred to as Z010011 (male parent, unpatented). 'Havana' was selected in 2009 by the inventor in 't Zand, The Netherlands as one flowering plant within the progeny of the stated cross.

The first act of asexual reproduction of 'Havana' by tissue culture was performed by the inventor in September of 2009 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in 14 cm pots in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Havana' which, in combination, distinguish this calla lily as a new and distinct cultivar:

1. Large, orange/red bicolored spathe; and
2. High inflorescence production.

Further, when compared to calla lily plant named 'Cancun' (U.S. Plant patent application Ser. No. 15/530,232), 'Cancun' has an upper surface spathe color that varies between Orange-Red Group RHS 32A and 34A and a lower surface spathe color that varies between Yellow Group RHS 13A and Orange-Red Group RHS 33B, whereas 'Havana' has an upper surface spathe color that varies between Orange-Red Group RHS 30A and N34B and a lower surface spathe color of Orange-Red Group RHS 34A.

TABLE 1

TABLE 1 provides similarities and differences of 'Havana' to its parents, *Zantedeschia sprengeri* 'Mercedes' and *Zantedeschia sprengeri* selection Z010011.

| 'Havana' | Similarities | Differences |
|---|---|---|
| 'Mercedes' | Number of inflorescences<br>Plant height | Spathe color<br>White leaf spots<br>Spathe shape |
| Z010011 | Leaf shape<br>Spathe shape | Spathe color<br>Number of inflorescences |

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

The Plant

Figure 1:
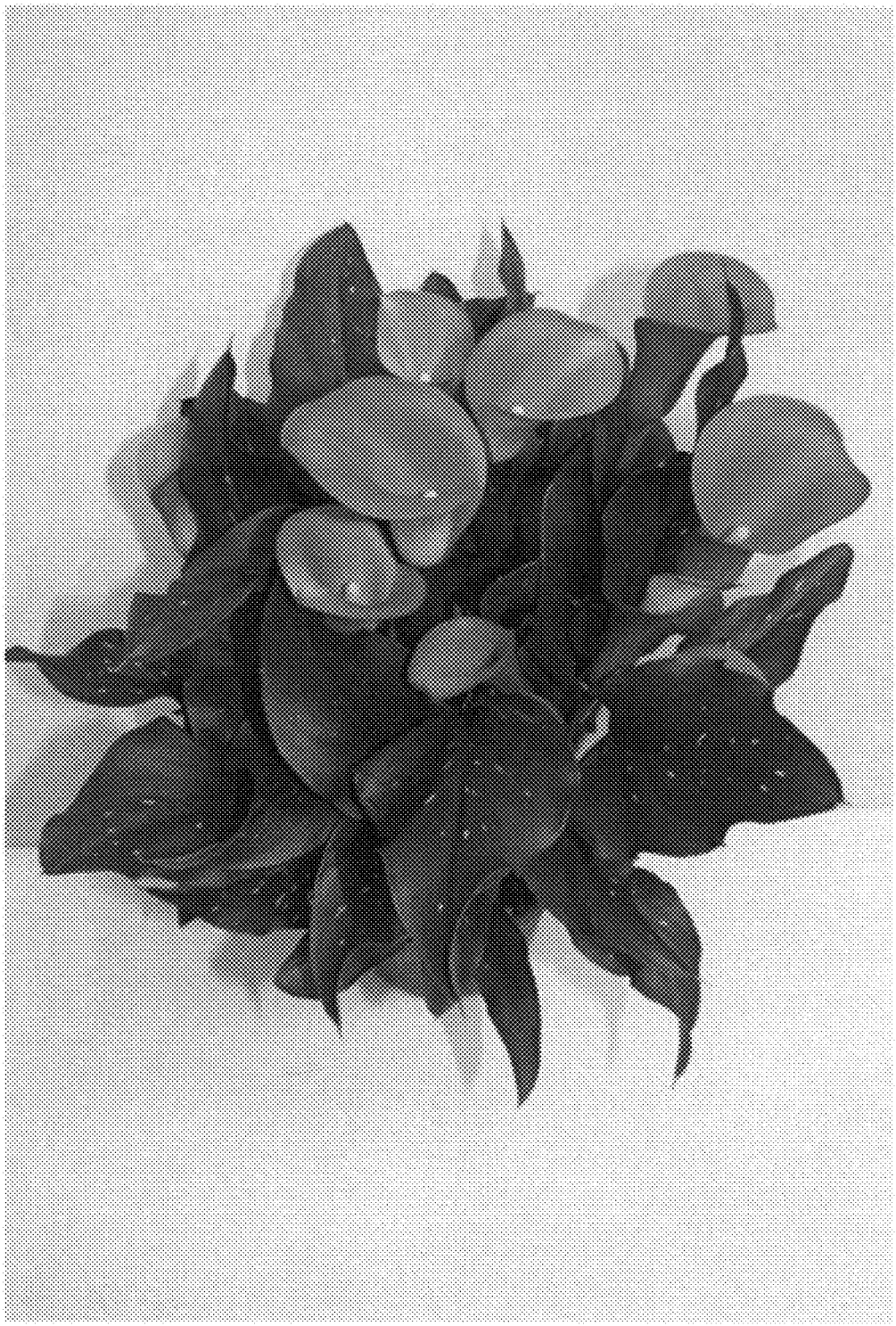
FIG. 1 is a photograph of a plant of the new variety.
Figure 2:
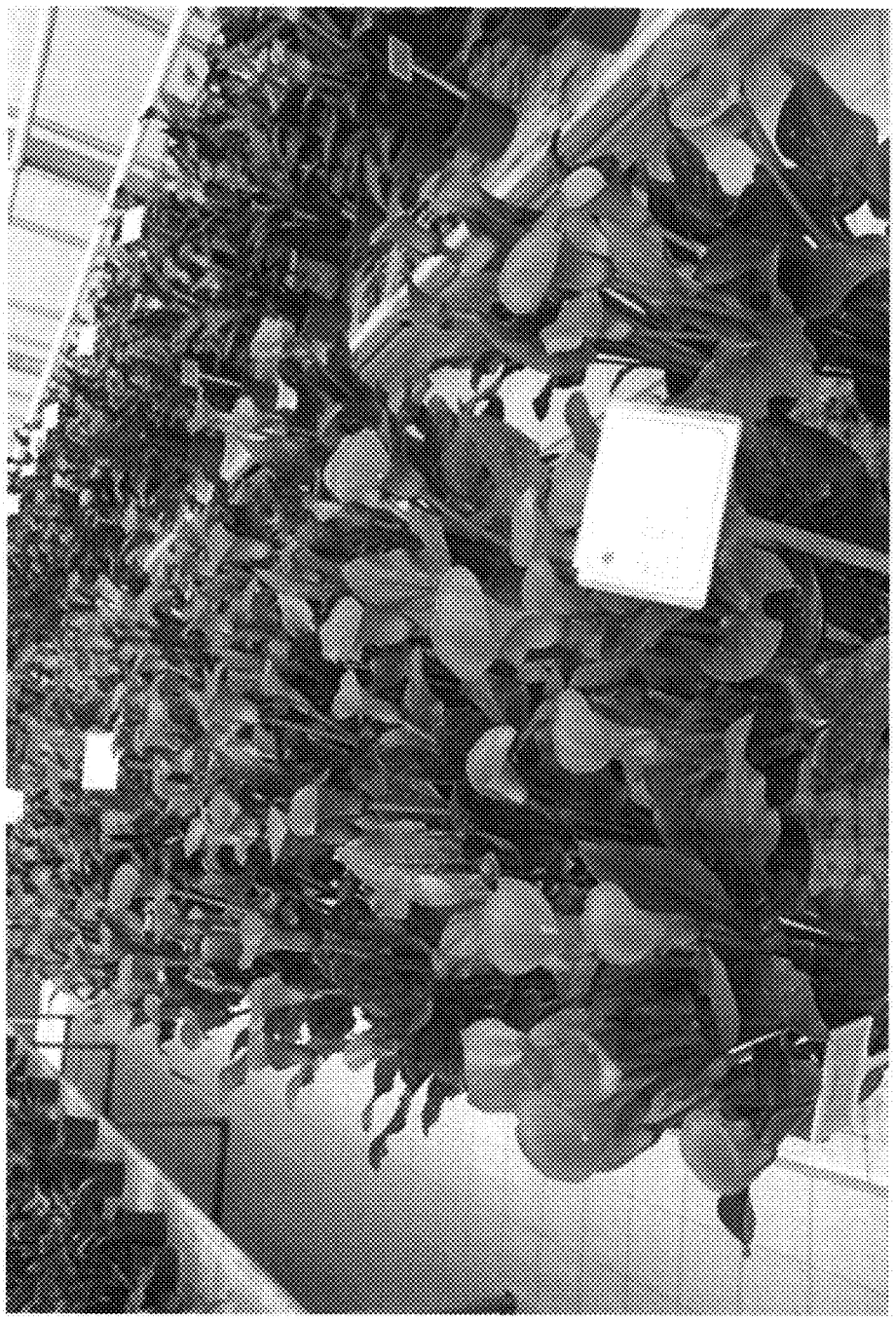
FIG. 2 is a photograph of a group of multiple plants of the new variety.

Size:
- *Height of the leaf canopy above the soil.*—17.5-45 cm.
- *Height of top of inflorescence above the soil.*—17-49 cm.
- *Diameter.*—8-50 cm.

Form: Erect.

Number of inflorescences per tuber:
- *Size* 14-16 *cm in diameter.*—3-7 inflorescences.
- *Size* 16-18 *cm in diameter.*—5-8 inflorescences.
- *Size* 18-20 *cm in diameter.*—5-10 inflorescences.

Branches:
- *Character.*—Many; like the variety 'Odessa' (U.S. Plant Pat. No. 18,833).
- *Color.*—Between Yellow-Green Group RHS 144A and 144B.

Leaves:
- *Size.*—Width: 1-15 cm. Length: 7-20.5 cm.
- *Number per plant.*—15-28.
- *Shape.*—Sagittate.
- *Color.*—Upper surface: Green Group RHS 137A to Yellow-Green Group RHS 147B, having transparent maculations between White Group RHS 155B and N155A. Lower surface: Green Group RHS 137A to Yellow-Green Group RHS 147B, having transparent maculations between White Group RHS 155B and N155A.
- *Apex.*—Apiculate.
- *Base.*—Truncate.
- *Margin.*—Undulate; having a color of Green Group RHS 143A.
- *Veins.*—Configuration: Pinnate. Color: Upper Surface: Green Group RHS 137A to Yellow-Green Group RHS 146A. Lower Surface: Yellow-Green Group RHS N144A to 146A.
- *Surface quality.*—Leathery.
- *Petiole.*—Length: 5-31 cm. Diameter: 8 mm. Color: The base is White Group RHS 155A, and the upper part is Yellow-Green Group RHS 144A.

Roots:
- *Color.*—White.
- *Branching.*—Similar to other *Zantedeschia* varieties.

The Inflorescence and Seeds

Spathe:
- *Size.*—Length (measured from opening to tip): 4.5-8.5 cm. Width: 3-7.5 cm. Height: 5.5-11 cm.
- *Color.*—Upper surface: Varies between Orange-Red Group RHS 30A and N34B. Lower surface: Orange-Red Group RHS 34A.
- *Vein color.*—Between Orange-Red Group RHS 34A and N34A.
- *Shape.*—Cupped.
- *Apex.*—Apiculate.
- *Margin.*—Entire.

Spadix:
- *Size.*—Length: 20-40 mm. Diameter: 2.5-10 mm.
- *Color.*—Between Yellow Group RHS 13A and Yellow-Orange Group RHS 15A.
- *Position relative to spathe.*—Upright.

Peduncle:
- *Size.*—Length: 24-40.5 cm. Diameter: 4-11 mm.
- *Color.*—The upper part is between Yellow-Green Group RHS 144A and 144B, and the lower part is Green-White Group RHS 157C.

Reproductive organs:
- *Location of female organs.*—Basal position of the spadix.
- *Location of male organs.*—Upper position of the spadix.
- *Perianth.*—Conspicuous.
- *Stamens.*—Presence: Not visible before pollen release. Number: More than 20. Pollen amount: Similar to 'Picasso' (U.S. Plant Pat. No. 15,282). Color: Between White Group RHS 155A and 155B.
- *Anther.*—Shape: Round. Length: Less than 1 mm. Color: Between Yellow Group RHS 13A and Yellow-Orange Group RHS 15A.
- *Filament.*—Length: Less than 1 mm. Color: Between White Group RHS 155A and 155B.
- *Pistils.*—Number: 15 to 30. Length beyond perianth: About 1 mm.
- *Stigma.*—Shape: Round. Size: Less than 1 mm.
- *Style.*—Length: Less than 1 mm. Color: Between Red-Purple Group RHS 59A and 59B.
- *Ovaries.*—Texture: Smooth. Length: Between 1 to 10 mm. Width: Between 1 to 10 mm. Color: Top color is between Yellow-Orange Group RHS 14A and 15A, bottom color is from White Group RHS 155B to Green-White Group RHS 157C.

Seeds:
- *Length.*—4-7 mm.
- *Width.*—3-6 mm.
- *Color.*—Between Yellow-Green Group RHS 150A and 151A.
- *Amount.*—Between 1-50.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July.

Lastingness: About two weeks on the plant.

Fragrance: None.

I claim:

1. A new and distinct variety of calla lily plant named 'Havana' as herein described and illustrated.

* * * * *